US010226166B2

(12) United States Patent
Fujitani et al.

(10) Patent No.: US 10,226,166 B2
(45) Date of Patent: Mar. 12, 2019

(54) ENDOSCOPE OPERATION PORTION AND ENDOSCOPE

(71) Applicant: OLYMPUS CORPORATION, Tokyo (JP)

(72) Inventors: Kiwamu Fujitani, Hachioji (JP); Keisuke Hatano, Koganei (JP); Takayasu Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/393,396

(22) Filed: Dec. 29, 2016

(65) Prior Publication Data

US 2017/0105602 A1     Apr. 20, 2017

Related U.S. Application Data

(63) Continuation of application No. PCT/JP2015/077285, filed on Sep. 28, 2015.

(30) Foreign Application Priority Data

Mar. 12, 2015   (JP) ................................. 2015-049800

(51) Int. Cl.
*A61B 1/00*     (2006.01)
*A61B 1/005*    (2006.01)
(Continued)

(52) U.S. Cl.
CPC ............ *A61B 1/0052* (2013.01); *A61B 1/005* (2013.01); *A61B 1/00066* (2013.01);
(Continued)

(58) Field of Classification Search
CPC ............ A61B 1/00066; A61B 1/00094; A61B 1/00068; A61B 1/005; A61B 1/0051;
(Continued)

(56) References Cited

U.S. PATENT DOCUMENTS

| 5,609,563 A | 3/1997 | Suzuki et al. |
| 2004/0073083 A1 | 4/2004 | Ikeda et al. |
| 2009/0287047 A1 | 11/2009 | Onoda et al. |

FOREIGN PATENT DOCUMENTS

| EP | 1927313 A1 | 6/2008 |
| JP | H03-097429 A | 4/1991 |

(Continued)

OTHER PUBLICATIONS

International Search Report dated Dec. 15, 2015 issued in PCT/JP2015/077285.
(Continued)

*Primary Examiner* — Ryan Henderson
(74) *Attorney, Agent, or Firm* — Scully, Scott, Murphy & Presser, P.C.

(57) ABSTRACT

An endoscope operation portion includes: an operation portion body provided being connected to a grasping portion; a joystick-type bending operation lever provided on a back side of the operation portion body, including a lever shaft body, and configured to perform a bending operation of a bending portion; and a suction button provided on a front side of the operation portion body so that an angle formed by an operation axis in a pressing-down operation direction relative to a central axis of the lever shaft body is an obtuse angle, and an intersection point between the central axis and the operation axis is positioned inside the operation portion body.

4 Claims, 8 Drawing Sheets

(51) Int. Cl.
*A61B 1/015* (2006.01)
*A61B 17/00* (2006.01)
*A61B 34/00* (2016.01)
*A61M 25/01* (2006.01)
*G02B 23/24* (2006.01)

(52) U.S. Cl.
CPC ...... *A61B 1/00068* (2013.01); *A61B 1/00094* (2013.01); *A61B 1/00128* (2013.01); *A61B 1/015* (2013.01); *A61M 25/0133* (2013.01); *A61M 25/0136* (2013.01); *G02B 23/24* (2013.01); *A61B 2017/003* (2013.01); *A61B 2017/00318* (2013.01); *A61B 2034/742* (2016.02)

(58) Field of Classification Search
CPC ... A61B 1/0052; A61B 1/0053; A61B 1/0055; A61B 1/0056; A61B 1/0057; A61B 1/0058; A61B 1/008; A61B 1/01; A61B 1/015; A61B 2017/003; A61B 2017/00318; A61B 2017/00323; A61B 2017/00327; A61B 34/74; A61B 2034/742; A61M 25/0133; A61M 25/0136; A61M 25/0147
See application file for complete search history.

(56) References Cited

FOREIGN PATENT DOCUMENTS

| JP | H04-256724 A | | 9/1992 | |
| JP | 06304122 A | * | 11/1994 | ........... A61B 1/0052 |
| JP | 2004-121413 A | | 4/2004 | |
| JP | 2006-149880 A | | 6/2006 | |
| JP | 2007-082842 A | | 4/2007 | |
| JP | 2008-036355 A | | 2/2008 | |
| WO | WO 2007/034732 A1 | | 3/2007 | |

OTHER PUBLICATIONS

Extended Supplementary European Search Report dated Jan. 18, 2018 in European Patent Application No. 15 88 4660.0.

* cited by examiner

ENDOSCOPE OPERATION PORTION AND ENDOSCOPE

CROSS REFERENCE TO RELATED APPLICATION

This application is a continuation application of PCT/JP2015/077285 filed on Sep. 28, 2015 and claims benefit of Japanese Application No. 2015-049800 filed in Japan on Mar. 12, 2015, the entire contents of which are incorporated herein by this reference.

BACKGROUND OF THE INVENTION

1. Field of the Invention

The present invention relates to an endoscope operation portion provided with a bending operation portion configured to operate a bending portion provided on an insertion portion of an endoscope to be inserted into a subject, and a function operating portion configured to operate endoscope functions such as suction, and the endoscope.

2. Description of the Related Art

Conventionally, in order to observe a position which is difficult to observe, inside a subject/object such as a living body and a structure, an endoscope which can be introduced into the subject/object has been widely used, for example, in a medical field and an industrial field.

An insertion portion of such an endoscope is provided with a bending portion for improving insertability into and observability inside the subject/object. The bending portion is bending-operated by operation means provided on an operation portion which is provided being connected to the insertion portion.

For example, in Japanese Patent Application Laid-Open Publication No. 2008-36355, a technique of an operation device as an endoscope operation portion provided with a joystick type operator is disclosed as operation means for performing a bending operation of a bending portion of an insertion portion. The conventional operation device is also provided with switches for operating air/water feeding, suction and the like in addition to the operator.

SUMMARY OF THE INVENTION

An endoscope operation portion of an aspect of the present invention includes: a grasping portion provided being connected to an insertion portion of an endoscope, the insertion portion including a bending portion; an operation portion body provided being connected to the grasping portion; a joystick-type bending operation lever provided on a back side of the operation portion body, including a lever shaft body, and configured to perform a bending operation of the bending portion; a suction button provided on a front side of the operation portion body so that an angle formed by an operation axis in a pressing-down operation direction relative to a central axis of the lever shaft body is an obtuse angle, and an intersection point between the central axis and the operation axis is positioned inside the operation portion body; and a plane portion provided on the front side of the operation portion body where the suction button is provided so as to be connected to the grasping portion, and formed so that an angle of the planar portion relative to the central axis of the lever shaft body is set to 90° or larger, and an intersection with the central axis is positioned on a surface.

An endoscope of an aspect of the present invention includes an endoscope operation portion including: a grasping portion provided being connected to an insertion portion of an endoscope, the insertion portion including a bending portion; an operation portion body provided being connected to the grasping portion; a joystick-type bending operation lever provided on a back side of the operation portion body, including a lever shaft body, and configured to perform a bending operation of the bending portion; a suction button provided on a front side of the operation portion body so that an angle formed by an operation axis in a pressing-down operation direction relative to a central axis of the lever shaft body is an obtuse angle, and an intersection point between the central axis and the operation axis is positioned inside the operation portion body; and a plane portion provided on the front side of the operation portion body where the suction button is provided so as to be connected to the grasping portion, and formed so that an angle of the planar portion relative to the central axis of the lever shaft body is set to 90° or larger, and an intersection with the central axis is positioned on a surface.

DETAILED DESCRIPTION OF THE PREFERRED EMBODIMENT(S)

Figure 1:
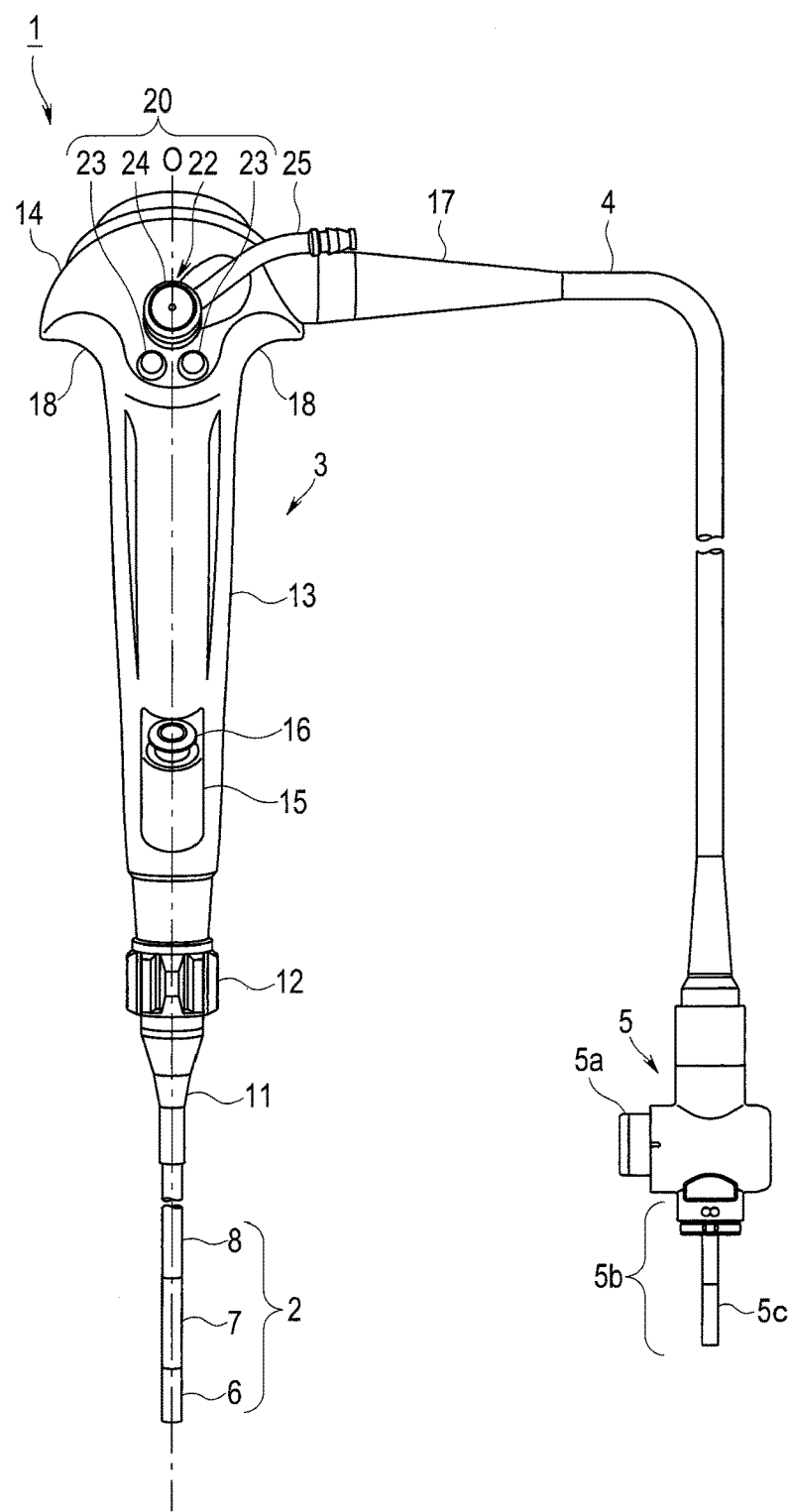
FIG. 1 is a front view showing an external appearance configuration of an endoscope according to an aspect of the present invention.

A preferable embodiment of the present invention will be described with reference to drawings. Note that, in each figure used in the description below, a different reduced scale is used for each component so that the component is shown in a size recognizable on the drawing, and the present invention is not limited only to the number of components, shapes of the components, a ratio of sizes of the components and relative positional relationships among the respective components shown in the figures. Further, in the description below, there may be a case where description is made on an assumption that upward and downward directions when facing a figure correspond to upper and lower parts of a component, respectively.

Figure 2:
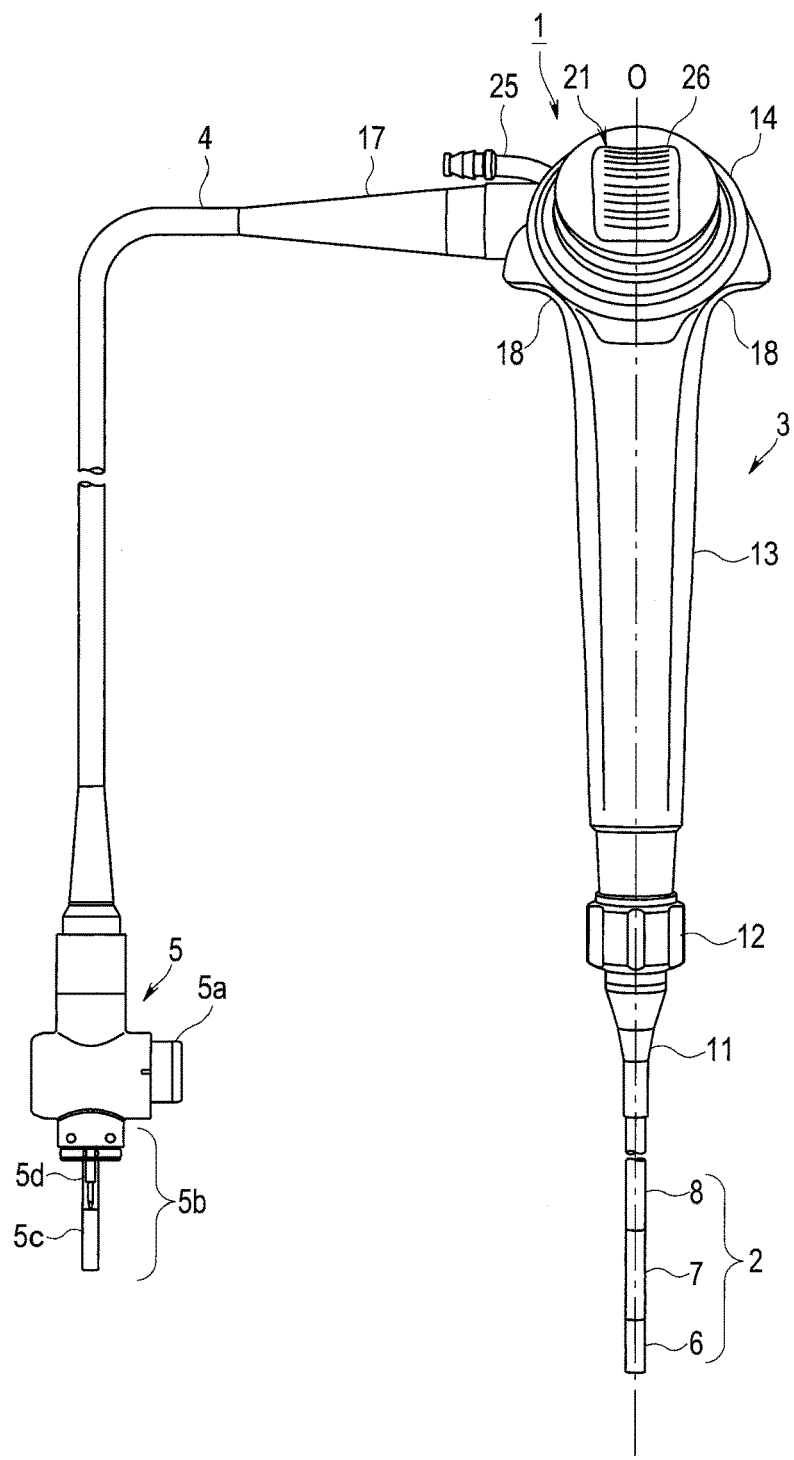
FIG. 2 is a rear view showing the external appearance configuration of the endoscope according to the aspect of the present invention.
Figure 3:
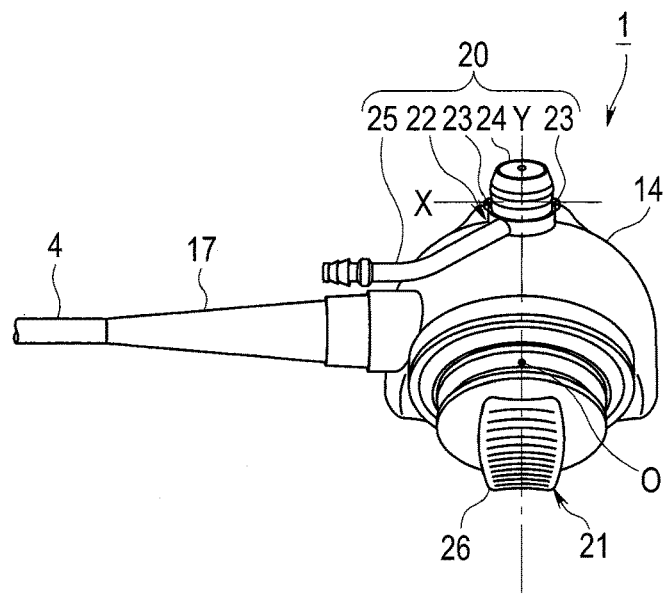
FIG. 3 is a top view showing the external appearance configuration of the endoscope according to the aspect of the present invention.
Figure 4:
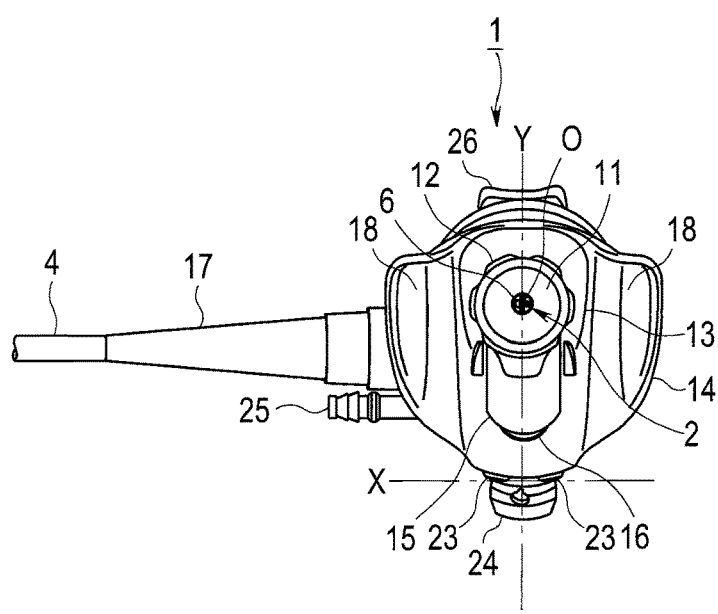
FIG. 4 is a bottom view showing the external appearance configuration of the endoscope according to the aspect of the present invention.
Figure 5:
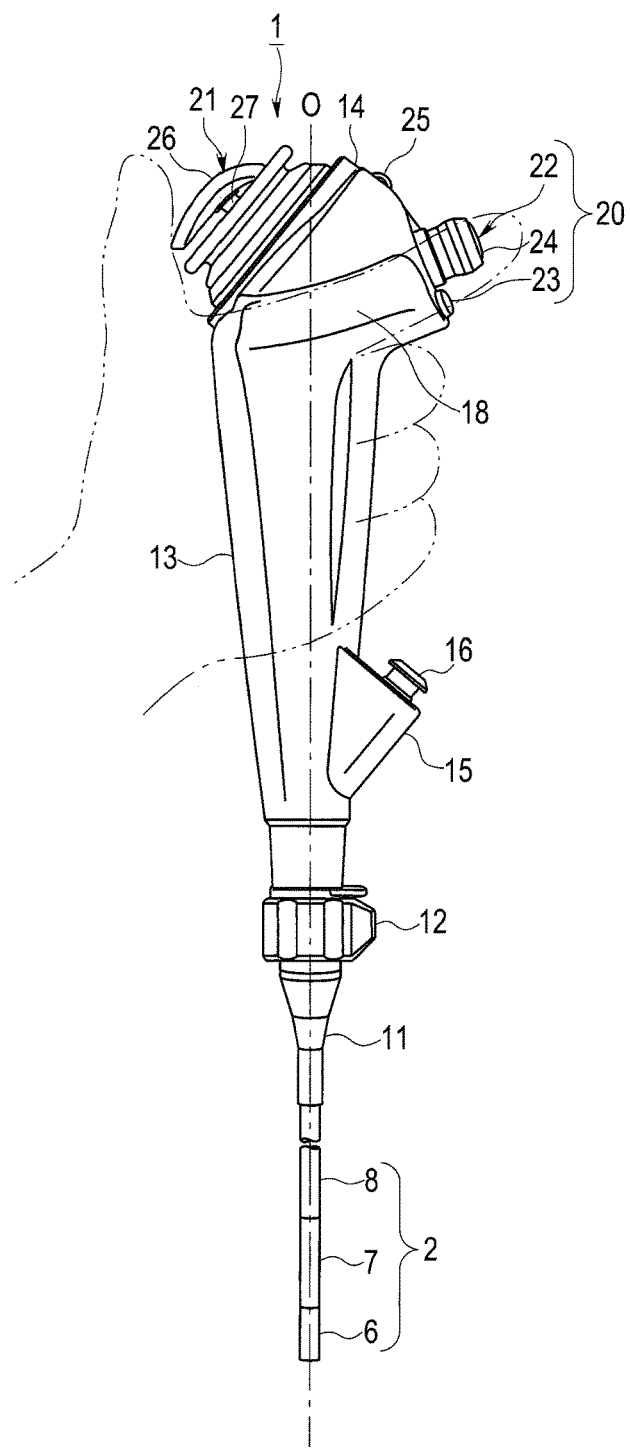
FIG. 5 is a right side view showing the external appearance configuration of the endoscope according to the aspect of the present invention.
Figure 6:
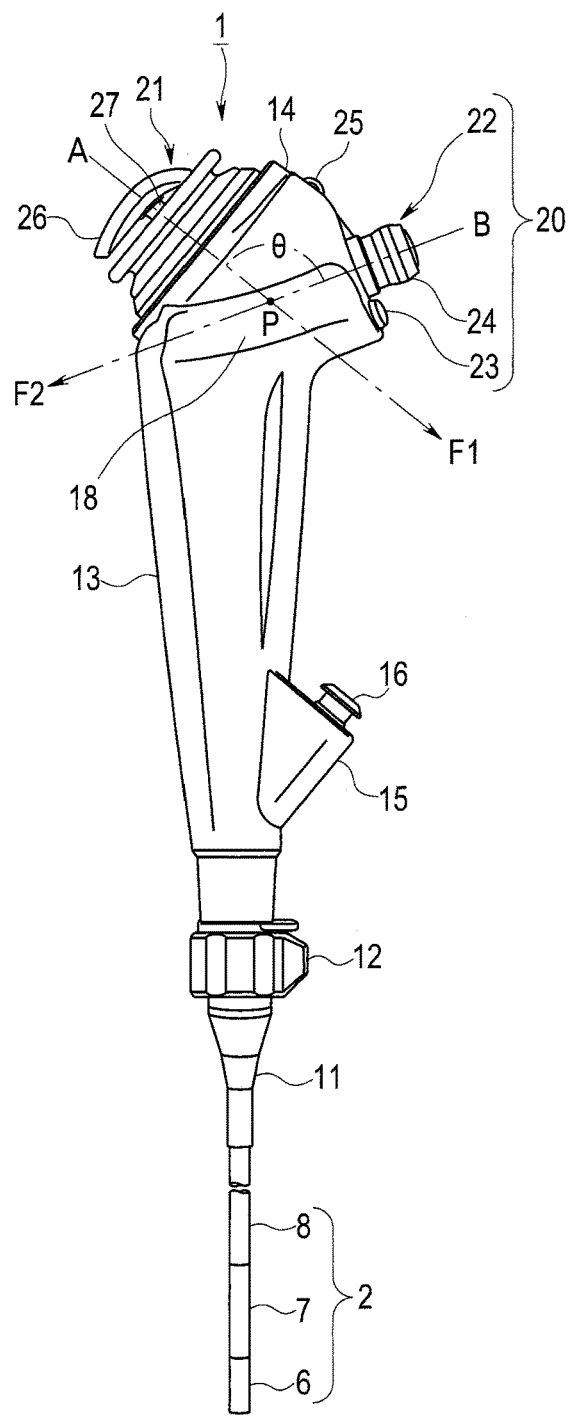
FIG. 6 is a right side view of the endoscope for illustrating arrangement of a bending operation lever and a suction button provided on an operation portion body when a bending portion is in a substantially straight state, according to the aspect of the present invention.
Figure 7:
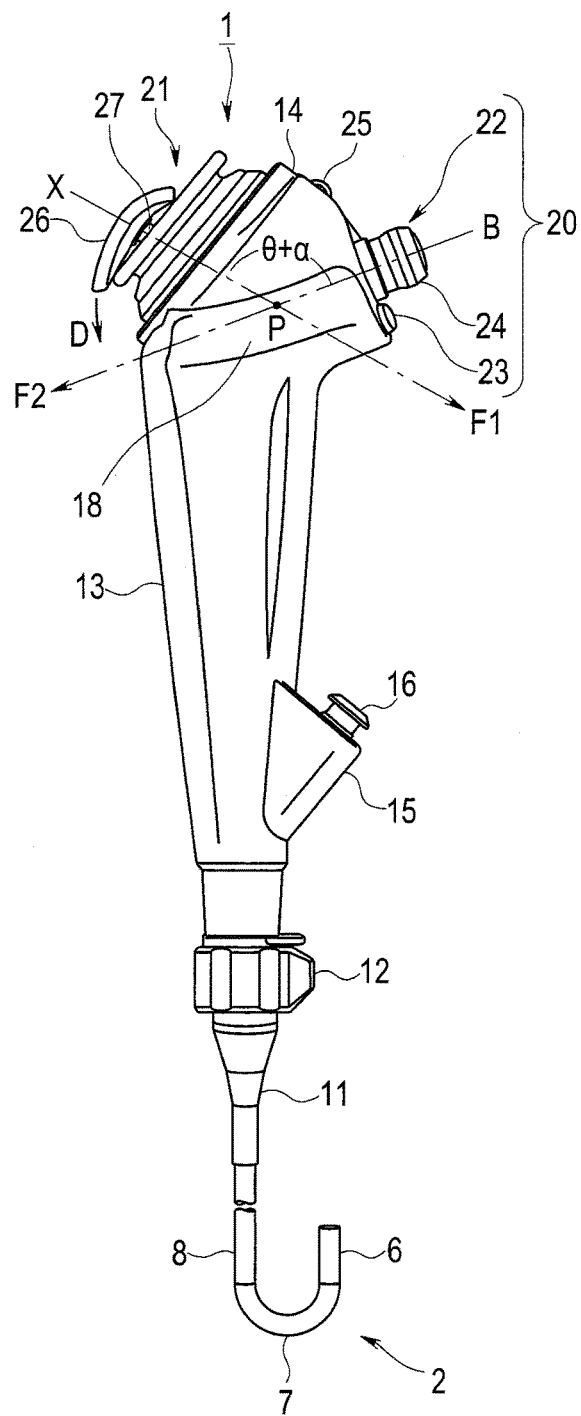
FIG. 7 is a right side view of the endoscope for illustrating arrangement of the bending operation lever and the suction button provided on the operation portion body when the bending portion is in a state of being bent upward, according to the aspect of the present invention.
Figure 8:
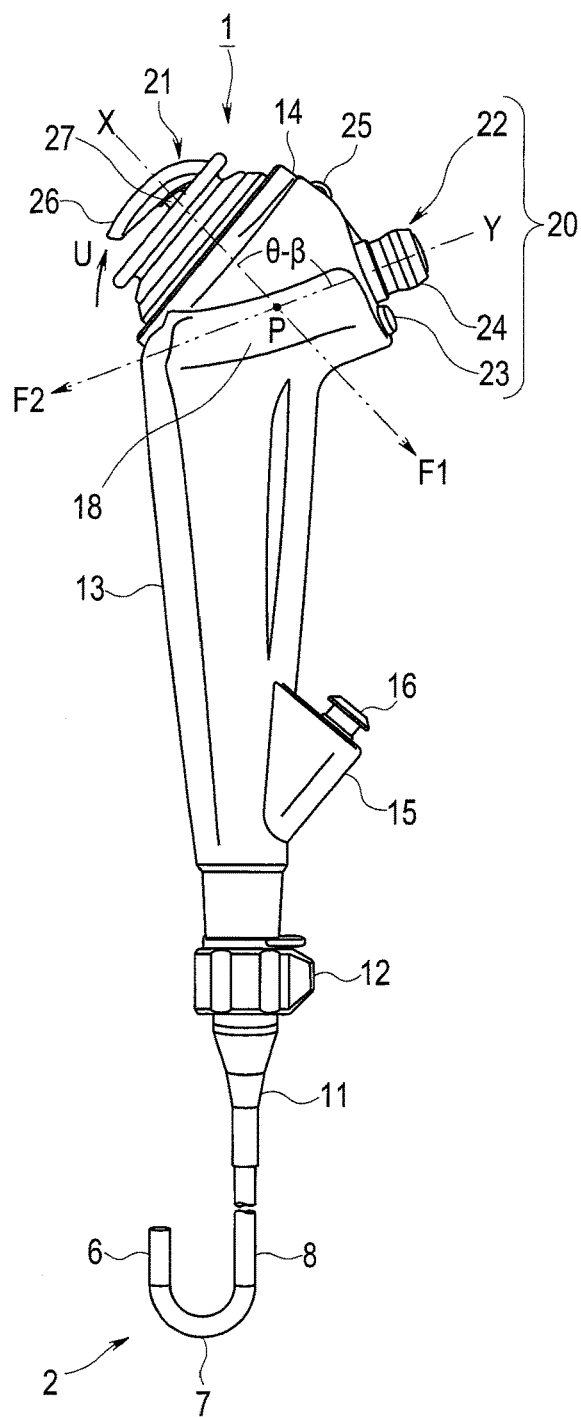
FIG. 8 is a right side view of the endoscope for illustrating arrangement of the bending operation lever and the suction button provided on the operation portion body when the bending portion is in a state of being bent downward, according to the aspect of the present invention.
Figure 9:
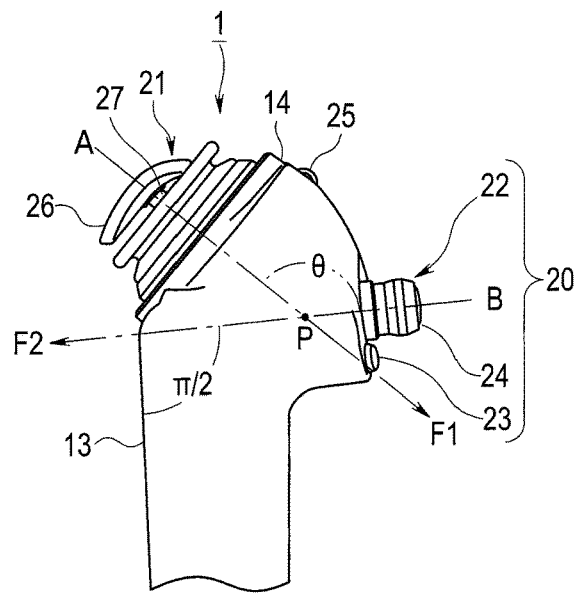
FIG. 9 is a right side view of the operation portion of a first modification of the aspect of the present invention.
Figure 10:
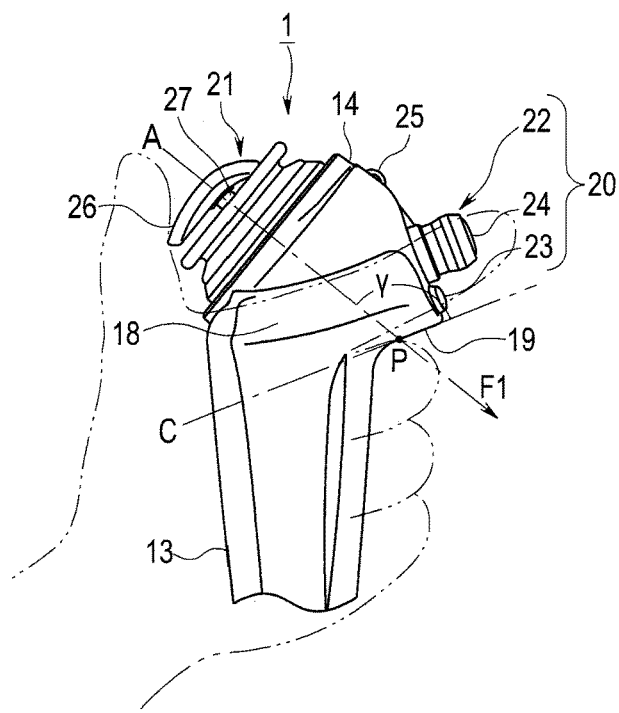
FIG. 10 is a right side view of the operation portion of a second modification of the aspect of the present invention.

First, an endoscope of an aspect of the present invention will be described below based on drawings. Note that FIG. 1 is a front view showing an external appearance configuration of an endoscope; FIG. 2 is a rear view showing the external appearance configuration of the endoscope; FIG. 3 is a top view showing the external appearance configuration of the endoscope; FIG. 4 is a bottom view showing the external appearance configuration of the endoscope; FIG. 5 is a right side view showing the external appearance configuration of the endoscope; FIG. 6 is a right side view of the endoscope for illustrating arrangement of a bending operation lever and a suction button provided on an operation portion body when a bending portion is in a substantially straight state; FIG. 7 is a right side view of the endoscope for illustrating arrangement of the bending operation lever and the suction button provided on the operation portion body when the bending portion is in a state of being bent upward; FIG. 8 is a right side view of the endoscope for illustrating arrangement of the bending operation lever and the suction button provided on the operation portion body when the bending portion is in a state of being bent downward; FIG. 9 is a right side view of the operation portion of a first modification; and FIG. 10 is a right side view of the operation portion of a second modification.

As shown in FIGS. 1 and 2, an endoscope 1 of the present embodiment is, for example, an electronic endoscope for bronchi or for urinary organs and is configured being provided with an insertion portion 2 formed in an elongated tube shape, an endoscope operation portion (hereinafter referred to as an operation portion) 3 provided being connected to a proximal end of the insertion portion 2, a universal cord 4 which is an endoscope cable extended from the operation portion 3, and an endoscope connector 5 arranged at a distal end of the universal cord 4.

The insertion portion 2 of the endoscope 1 is configured with a flexible tubular member including a distal end portion 6, a bending portion 7 and a flexible tube portion 8 which are connectedly provided in that order from a distal end side.

In the distal end portion 6 of the insertion portion 2, an objective optical system, an image pickup unit including an image sensor such as a CCD and a CMOS, an illumination optical system configured to radiate illuminating light transmitted by a light guide bundle, a channel pipe configured to connect and retain a treatment instrument channel, and the like are arranged though they are not shown here.

Note that the endoscope 1 is not limited to an electronic endoscope provided with an image pickup unit but may be configured with use of an image fiber.

The bending portion 7 of the insertion portion 2 is configured so that the bending portion 7 can be caused to be actively bent in all directions around an insertion axis O including up-down/right-left directions according to an operation input by a user who is an operating person of the operation portion 3.

The flexible tube portion 8 of the insertion portion 2 is configured with a flexible tubular member which can be passively bent. Inside the flexible tube portion 8, an image pickup cable, the light guide bundle, the treatment instrument insertion channel and an air/water feeding tube are inserted (none of them is shown).

The operation portion 3 of the endoscope 1 is configured including a bending preventing portion 11 connected to the flexible tube portion 8 in a state of covering a proximal end of the flexible tube portion 8, an insertion portion rotating dial 12 provided on a proximal end side of the bending preventing portion 11 and configured to be capable of freely adjusting a rotational position of the insertion portion 2 around the insertion axis O, a grasping portion 13 connectedly provided on a proximal end side of the insertion portion rotating dial 12 and configured so that the user or the like can grasp by hand, and an operation portion body 14 connectedly provided on a proximal end side of the grasping portion 13.

Note that, in the present embodiment, a direction around the insertion axis O as a longitudinal axis of the operation portion 3 (in description below, the longitudinal axis of the operation portion 3 will be described as being the same as the insertion axis O) and the like are defined on a basis of a state that the user or the like grasps the grasping portion 13 (see FIG. 5). More specifically, the up-down/right-left directions (a front, a back, right and left sides and the like) on a basis of the user or the like grasping the grasping portion 13 are defined for the operation portion 3.

The grasping portion 13 is formed in a symmetrical shape relative to the insertion axis O so that the user or the like can grasp the grasping portion 13 similarly by either of left and right hands.

On the front on a distal end side of the grasping portion 13, a treatment instrument inserting portion 15 is provided. The treatment instrument inserting portion 15 is configured being provided with a treatment instrument insertion opening 16 through which various kinds of treatment instruments not shown are to be inserted.

Inside the operation portion 3, the treatment instrument insertion channel communicates with the treatment instrument insertion opening 16 via a branching member (neither of the treatment instrument insertion channel nor the branching member is shown). Further, for example, a disposable forceps plug not shown, which is a cover member for blocking the treatment instrument insertion opening 16, is attachable to and detachable from the treatment instrument inserting portion 15.

The operation portion body 14 is configured with a hollow member forming a substantially partially spherical shape swelled mainly in right and left side directions and forward, on the proximal end side of the grasping portion 13. On a front side of the operation portion body 14, operation buttons 20 for executing a suction function, various optical system functions and the like of the endoscope 1 are arranged.

On the other hand, on a back side of the operation portion body 14, a bending operation lever 21, which is an operator as bending operation means for performing a bending operation of the bending portion 7, is arranged. Furthermore, from one side (for example, a left side) of the operation portion body 14, the universal cord 4 is extended via a cable bending preventing portion 17.

Here, a right-left shape of the operation portion body 14 is a swelled shape symmetrical relative to the insertion axis O. On right and left sides on a distal end side of the operation portion body 14, guiding recess portions 18 for guiding a forefinger or the like of the user or the like grasping the grasping portion 13 to the operation buttons 20 are formed, respectively.

The universal cord 4 is a composite cable which reaches from the distal end portion 6 side to the operation portion 3 through an inside of the insertion portion 2 and in which various signal lines including the image pickup cable, which extend from the operation portion 3, the light guide bundle and the air/water feeding tube into which fluid for air/water feeding is caused to flow in (none of which is shown) are inserted inside.

The endoscope connector 5 provided at an end portion of the universal cord 4 includes an electric connector portion 5a and a light source connector portion 5b connected to a light source apparatus, which is an external apparatus not shown.

Note that a video processor, which is an external apparatus not shown, or a connector of an extendedly provided electric cable is attachably and detachably connected to the electric connector portion 5a. Further, a light guide connector portion 5c in which the light guide bundle is accommodated and an air/water feeding connector portion 5d are arranged in the light source connector portion 5b.

Next, a configuration of each portion of the operation portion body 14 will be described in more detail.

As shown in FIGS. 3 and 4, for example, the operation buttons 20 are configured with, for example, a disposable suction valve 22 attachably and detachably fitted to the operation portion body 14, and two button switches 23 to which an arbitrary function, for example, a release button can be selectively assigned from among various functions related to the endoscope 1.

Note that the suction valve 22 is configured including a suction button 24 as an operation input member, and a tube connection portion 25 to which a suction tube extended from an endoscope aspirator, which is an external apparatus not shown, is connected.

The bending operation lever 21 provided on the back side of the operation portion body 14 is configured, for example, with a so-called joystick type lever which is tillable in all the directions including the up-down/right-left directions. A tip portion of a lever shaft body 27 (see FIG. 5) of the bending operation lever 21 is provided with a finger touch portion 26 which a thumb of the user or the like can be brought in contact with.

The finger touch portion 26 is arranged substantially at a center in a right-left width direction on the back side of the operation portion body 14 so as to be overlapped with the insertion axis O and a virtual line Y (see FIG. 3). That is, the finger touch portion 26 of the bending operation lever 21 and the suction button 24 of the suction valve 22 are arranged substantially at the center in the right-left width direction on the front side or the back side of the operation portion body 14.

Note that the bending operation lever 21 is provided on a more proximal end side (an upward side in FIG. 5) of the operation portion 3 than a base of the thumb so that the user or the like can operate the finger touch portion 26 by the thumb of the hand grasping the grasping portion 13.

Further, inside the operation portion 3, a bending operation mechanism not shown is coupled with a proximal end side of the bending operation lever 21. The bending operation lever 21 is capable of causing the bending portion 7 to perform a bending operation in an arbitrary direction via a pulling operation of each pulling wire by the bending operation mechanism.

Note that bending directions of the bending portion 7 for operation directions are set so that the bending portion 7 bends upward by the bending operation lever 21 being tilted directly downward and bends downward by the bending operation lever 21 being tilted directly upward. Further, operation directions of the bending operation lever 21 for causing the bending portion 7 to bend in the right and left directions correspond to directions of the bending operation lever 21 being tilted right and left.

By the way, as for the operation directions of the bending operation lever 21, since the bending operation lever 21 can be tilted in all the directions including the up-down/right-left directions, directly upward and directly downward directions and directly right-left directions are difficult to recognize when performing an operation.

Therefore, on the endoscope 1 of the present embodiment, the suction button 24 of the suction valve 22 is arranged substantially at the center in the right-left width direction on the front side of the operation portion body 14 so as to be overlapped with the insertion axis O and the virtual line Y in the endoscope 1 of the present embodiment as described above, and the endoscope 1 can be operated in the directly upward direction by tilting the finger touch portion 26 of the bending operation lever 21 to the front side of the operation portion body 14 in a direction toward the suction button 24, and, on the contrary, can be operated in the directly downward direction by tilting the finger touch portion 26 on an opposite side of the front direction of the operation portion body 14 in the direction toward the suction button 24.

Further, on the endoscope 1, the two button switches 23 are arranged side by side on a virtual line X in the right-left width direction of the operation portion body 14 and arranged so as to be symmetrical, with the virtual line Y passing through the insertion axis O and dividing the operation portion body 14 into two between the two button switches 23, as described above, and the endoscope 1 can be operated in a directly lateral direction by tilting the finger touch portion 26 of the bending operation lever 21 in a direction along the two button switches 23.

Thus, the endoscope 1 is configured so that the suction button 24 and the two button switches 23 serve as up-down/right-left indicator portions to make it easy to recognize the up-down/right-left operation directions of the bending operation lever 21.

Note that parting lines and lateral lines of the grasping portion 13, the operation portion body 14 and the like of the operation portion 3 may be up-down/right-left indicator portions in order to make it easy to recognize the up-down/right-left operation directions of the bending operation lever 21. Furthermore, a cross line to be an up-down/right-left operation direction indicator portion may be provided on the finger touch portion 26 of the bending operation lever 21.

Here, arrangement of the bending operation lever 21 and the suction button 24 will be described in detail.

As shown in FIG. 6, the lever shaft body 27 of the bending operation lever 21 has a central axis A.

An operation axis B in a pressing-down direction of the suction button 24 is set so that an angle $\theta$ formed relative to the central axis A of the lever shaft body 27 of the bending operation lever 21 is to be an obtuse angle when the bending portion 7 is in a substantially straight state when not being operated.

Further, an intersection point P between the central axis A of the lever shaft body 27 of the bending operation lever 21 and the operation axis B of the suction button 24 is set to be positioned inside the operation portion body 14 of the operation portion 3.

By the lever shaft body 27 of the bending operation lever 21 and the suction button 24 of the suction valve 22 being provided as described above, a stress F1 by the operating person pressing the finger touch portion 26 of the bending operation lever 21 with his thumb so that the bending operation lever 21 does not move and a stress F2, which is pressing force of pressing down the suction button 24, are in opposite directions, and the angle $\theta$ formed by the directions in which the stresses F1 and F2 occur (the central axis A and the operation axis B) becomes an obtuse angle when the bending portion 7 keeps the substantially straight state when not being operated.

Further, as shown in FIG. 7, an angle θ+α formed by the operation axis B in the direction of pressing down the suction button 24 relative to the central axis A of the lever shaft body 27 of the bending operation lever 21 is set to become an obtuse angle when the bending portion 7 is bending-operated upward.

In this state also, the intersection point P between the central axis A of the lever shaft body 27 of the bending operation lever 21 and the operation axis B in the direction of pressing down the suction button 24 is positioned inside the operation portion body 14 of the operation portion 3.

That is, here also, the stress F1 by the operating person pressing the finger touch portion 26 of the bending operation lever 21 with his thumb so that the bending operation lever 21 does not move and the stress F2, which is the pressing force of pressing down the suction button 24, are in opposite directions, and the angle θ+α formed by the directions in which the stresses F1 and F2 occur (the central axis A and the operation axis B) becomes an obtuse angle when the bending portion 7 keeps the state of being bending-operated upward.

Furthermore, as shown in FIG. 8, an angle θ−β formed by the operation axis B in the direction of pressing down the suction button 24 relative to the central axis A of the lever shaft body 27 of the bending operation lever 21 is also set to become an obtuse angle when the bending portion 7 is bending-operated downward.

In this state also, the intersection point P between the central axis A of the lever shaft body 27 of the bending operation lever 21 and the operation axis B in the direction of pressing down the suction button 24 is positioned inside the operation portion body 14 of the operation portion 3.

That is, here also, the stress F1 by the operating person pressing the finger touch portion 26 of the bending operation lever 21 with his thumb so that the bending operation lever 21 does not move and the stress F2, which is the pressing force of pressing down the suction button 24, are in opposite directions, and the angle θ−β formed by the directions in which the stresses F1 and F2 occur (the central axis A and the operation axis B) becomes an obtuse angle when the bending portion 7 keeps the state of being bending-operated downward.

Thus, the bending operation lever 21 and the suction button 24 are arranged so that, even if the bending portion 7 is in the states of bending upward and downward, the stress F1, which occurs on the bending operation lever 21, and the stress F2, which is pressing-down force pressing down the suction button 24, in opposite directions and along the central axis A and the operation axis B which cross at an obtuse angle and the intersection point P of which exists in the operation portion body 14, respectively, offset each other when the bending states are kept.

In addition, since the grasping portion 13 of the operation portion 3 is grasped by the operating person's hand, it is possible to prevent the bending operation lever 21 from being shifted when the suction button 24 is pressed down.

Therefore, the endoscope 1 of the present embodiment is such that, when performing a suction operation, the bending operation lever 21 is not easily shifted, and, thereby, it is possible to prevent the distal end portion 6 from being shifted by the bending portion 7 moving and it is possible to keep a state of being fixed in a desired field-of-view direction.

Therefore, the endoscope 1 is configured such that it is possible to, by preventing the bending operation lever 21 from being shifted when operating the bending operation lever 21, which is an operator for a bending operation, and the suction button 24, which is a switch for an endoscope function, in order for the bending portion 7 to keep a desired bending operation, prevent the distal end portion 6 from being shifted.

Note that, especially an operation of bending the bending portion 7 of the endoscope 1 upward from the substantially straight state when the bending portion 7 not being operated is frequently performed. Therefore, it is sufficient if the bending portion 7 can keep the substantially straight state when not being operated and the state of bending upward.

That is, the endoscope 1 is not necessarily required to include the state of bending downward, and the bending operation lever 21 and the suction button 24 described above can be arranged at least when the bending portion 7 is in the substantially straight state when not being operated and the state of bending upward.

(First Modification)

As shown in FIG. 9, in the endoscope 1, by causing the operation axis B in the direction of pressing down the suction button 24 to be substantially at a right angle π/2 relative to the back, which is a side where the bending operation lever 21 is provided on the operation portion body 14, on the grasping portion 13 of the operation portion 3, the stress F2, which is the pressing force of pressing down the suction button 24 is suppressed by a palm of the operating person grasping the grasping portion 13.

By adopting such a configuration, the endoscope 1 can be such that it is possible to prevent the bending operation lever 21 from being shifted when the suction button 24 is pressed down more.

(Second Modification)

As shown in FIG. 10, on the endoscope 1, a planar portion 19 is formed on a lower end side, which is a distal end side of a projection portion where the operation buttons 20 are provided, on the front side of the operation portion body 14 provided being connected to the grasping portion 13, and an angle γ formed by the planar portion 19 indicated by a virtual line C relative to the central axis A of the lever shaft body 27 of the bending operation lever 21 is set to an obtuse angle larger than 90° including 90°.

Note that, even in a state of the bending portion 7 being bent upward and downward to the maximum, the angle γ formed by the planar portion 19 relative to the central axis A of the lever shaft body 27 of the bending operation lever 21 is set to an obtuse angle larger than the right angle (90°) including the right angle (90°). That is, the formed angle γ is set to be equal to or larger than 90° (γ≥90°).

By adopting such a configuration, in the endoscope 1, since a finger of the operating person grasping the grasping portion 13, here, a middle finger comes into contact with the planar portion 19, a stress along the central axis A which occurs when the bending operation lever 21 is operated is received by the finger in contact with the planar portion 19; and, thereby, the operation portion 3 becomes stable, and it is possible to prevent the bending operation lever 21 from being shifted.

Therefore, in the endoscope 1 of the present modification also, it is possible to prevent the bending operation lever 21 from being shifted when the suction button 24 is pressed down for a suction operation, prevent the distal end portion 6 from being shifted by the bending portion 7 moving, and keep the state of being fixed in a desired field of view direction.

The invention described in each embodiment above is not limited to the embodiment and modifications, and, additionally, various variations can be made within a range not departing from the spirit of the invention at a stage of practicing the invention. Furthermore, each embodiment above includes inventions at various stages, and various inventions can be extracted by appropriately combining a plurality of disclosed constituent features For example, even if some constituent features are deleted from all constituent features shown in each embodiment, a configuration obtained after deleting the constituent features can be extracted as an invention if the stated problem can be solved, and the stated advantageous effects can be obtained.

What is claimed is:

1. An endoscope operation portion comprising:
   a grasping portion having a distal end configured to be connected to an insertion portion of an endoscope, the insertion portion comprising a bending portion;
   an operation portion body connected to a proximal end of the grasping portion, the operation portion body including a first side, a second side, the second side being an opposite side of the first side, the operation portion body further including a third side, and a fourth side, the fourth side being an opposite side of the third side;
   a joystick-type bending operation lever provided on the second side of the operation portion body, the joystick-type bending operation lever including a lever shaft body, the joystick-type bending operation lever being configured to perform a bending operation of the bending portion;
   a suction button provided on the first side of the operation portion body so that an angle formed by a pressing-down operation direction of the suction button relative to a central axis of the lever shaft body is an obtuse angle, and an intersection point between the central axis and the pressing-down operation direction is positioned inside the operation portion body; and
   a first recess portion formed on the third side of the operation portion body, the first recess being configured to guide a finger of an operator grasping the grasping portion;
   a second recess portion formed on the fourth side of the operation portion body, the second recess being configured to guide a finger of the operator grasping the grasping portion; and
   a planar surface formed distally with respect to the first and second recess portions, the planar surface being formed on the first side so as to connect the first and second recess portions,
   wherein the planar surface is formed so that an angle of the planar surface relative to the central axis of the lever shaft body is set to 90° or larger, and the planar surface intersects with the central axis.

2. The endoscope operation portion according to claim 1, wherein at least when the bending portion is in a straight state when not being operated by the lever shaft body and in an upward bending state, the angle formed by the pressing-down operation direction relative to the central axis is an obtuse angle.

3. The endoscope operation portion according to claim 1, wherein the angle formed by the pressing-down operation direction is substantially at a right angle relative to the second side of the operation portion body.

4. An endoscope comprising the endoscope operation portion according to claim 1.

* * * * *